United States Patent [19]

Bost et al.

[11] 3,953,527

[45] Apr. 27, 1976

[54] HYDROXYLATION OR AROMATIC COMPOUNDS

[75] Inventors: Pierre Bost; Michel Constantini, both of Lyon; Michel Jouffret, Francheville-le-Bas; Guy Lartigau, Lyon, all of France

[73] Assignee: Rhone-Poulenc, S.A., Paris, France

[22] Filed: May 1, 1973

[21] Appl. No.: 356,121

[30] Foreign Application Priority Data

May 3, 1972  France ............................ 72.15697

[52] U.S. Cl. .......................... 260/621 G; 260/613 D
[51] Int. Cl.² .................. C07C 39/08; C07C 39/06; C07C 43/20
[58] Field of Search .................... 260/613 D, 621 G

[56] References Cited
UNITED STATES PATENTS

| | | | |
|---|---|---|---|
| 3,376,351 | 4/1968 | Amedjian et al. | 260/613 D |
| 3,377,386 | 4/1968 | Chafetz | 260/621 G |
| 3,453,332 | 7/1969 | Vesley et al. | 260/613 D |
| 3,461,170 | 8/1969 | Schmerling | 260/613 D |
| 3,514,490 | 5/1970 | Marlard | 260/621 G |

FOREIGN PATENTS OR APPLICATIONS 2,071,464  9/1971  France ............................ 260/613 D

OTHER PUBLICATIONS

Ogata et al., Chem. Abstract, 74, 76134v (1971).

*Primary Examiner*—James O. Thomas, Jr.
*Assistant Examiner*—Nicky Chan
*Attorney, Agent, or Firm*—Stevens, Davis, Miller & Mosher

[57] ABSTRACT

Aromatic compounds of formula

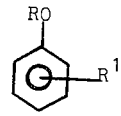

in which R and R¹ are independently hydrogen or $C_1-C_4$ alkyl are hydroxylated with hydrogen peroxide and a phosphorus compounds, which is a phosphoric acid, ester thereof, halogenophosphoric acid, ester thereof, phosphorus pentoxide, phosphorus halide or oxyhalide, in the absence of acid of pK < −0.1.

3 Claims, No Drawings

HYDROXYLATION OR AROMATIC COMPOUNDS

This invention relates to a process for the hydroxylation of aromatic compounds.

Numerous processes for the oxidation of phenols and phenol ethers with hydrogen peroxide combined with metal salts or by means of organic peracids (formed from hydrogen peroxide and a carboxylic acid) have been described. Depending on the particular cases, these processes have made it possible to introduce a hydroxyl radical into the ring of the aromatic compound or have caused a more or less extensive oxidation of this ring, ranging from the production of quinones to the opening of the benzene ring with formation of degradation products [ see A. CHWALA et al., J. Prakt. Chem., 152, 46 (1939); G. G. HENDERSON, J. Chem. Soc., 91, 1659 (1910); S. L. FRIESS et al., J. Chem. Soc., 74, 1305 (1952); H. FERNOLZ, Ber., 87, 578 (1954); H. DAVIDGE et al., J. Chem. Soc., 1958, 4569; and J. D. McCLURE et al., J. Org. Chem., 27, 627 (1962) ]. However, either because of low productivities of hydroxylation products (use of large amounts of reagents), or because of insufficient yields, none of the processes described in the prior art mentioned above was of value, more particularly for the preparation of diphenols such as hydroquinone and pyrocatechol or of alkoxyphenols such as quiacol and p-methoxyphenol.

Various processes of very great industrial value have also been proposed for the hydroxylation of phenols and their ethers. Thus French Pat. No. 1,479,354 describes a process for the preparation of hydroquinone and pyrocatechol by hydroxylation of phenol by means of an aliphatic peracid (especially performic acid), the degree of conversion of the phenol being limited to 30% at the most. The best yields of diphenols relative to the hydrogen peroxide employed are obtained when the reaction is carried out in the presence of phosphoric acid (this yield then reaches a value of 73.5% for an 8.7% degree of conversion of the phenol). On replacing phosphoric acid by a mixture of pyrophosphoric acid and phosphorus pentoxide, Y. OGATA et al., C. A. 74, 76,134 obtained similar results.

These processes are of a certain industrial value and they show obvious technical progress compared with those proposed previously, but means have been sought for improving them by carrying out the direct hydroxylation of aromatic compounds by means of hydrogen peroxide alone by a process which excludes the formation of an organic peracid.

For this purpose, it has been proposed, in French Pat. No. 2,071,464, to replace the hydrogen peroxide/organic acid/phosphoric acid hydroxylation system by hydrogen peroxide alone in the presence of traces of a strong acid of pK in water less than —0.1, and preferably in the presence of an agent for complexing the metal ions which may be present in the mixture, such as orthophosphoric acids and polyphosphoric acids (for example, pyrophosphoric acid). It has now be found, unexpectedly, that it is possible to carry out the hydroxylation of aromatic compounds by means of hydrogen peroxide without requiring the presence of strong acids of pK in water less than —0.1, when certain phosphorus-containing compounds are used in conjunction with hydrogen peroxide.

The present invention provides a process for the preparation of a hydroxylated aromatic compound, which comprises hydroxylating a compound of the general formula:

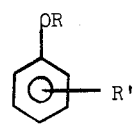
(I)

in which each of R and R', which ar the same or different, represents a hydrogen atom or an alkyl radical containing 1 to 4 carbon atoms, with hydrogen peroxide in the presence of at least one phosphorus-containing compound, which is a phosphoric acid or ester thereof, halogenophosphoric acid or ester thereof, phosphorus pentoxide or phosphorus halide or oxyhalide, and in the absence of an acid of pK < —0.1.

In the above formula, R and R' can be methyl, ethyl, or one of the various propyl or butyl radicals.

Orthophosphoric acid and condensed phosphoric acids, are preferred phosphorus containing compounds. By the term "condensed phosphoric acids" is meant in this specification acids in which the molar ratio of water to phosphorus pentoxide, theoretically necessary for their preparation, is less than 3, the value at which orthophosphoric acid is obtained. More preferred are condensed acids in which the ratio is less than 2.5. Specific examples of condensed acids are pyrophosphoric acid $H_4P_2O_7$ (ratio $H_2O/P_2O_5 = 2$), metaphosphoric acid $HPO_3$ (ratio $H_2O/P_2O_5 = 1$) and its polymers (tri- and tetra-metaphosphoric acids), and polyphosphoric acids (ratio $H_2O/P_2O_5$ between 1 and 2). These various acids can be obtained especially by heating orthophosphoric acid or by mixing phosphorus pentoxide with orthophosphoric acid and/or water (see KIRK-OTHMER - Encyclopedia of Chemical Technology, Sec. Ed. Volume 15, p. 241 et seq.). The various acid mentioned above can be used as mixtures with one another or with phosphorus pentoxide. The use of a mixture of $H_3PO_4$ and of $P_2O_5$ in varying proportions can lead to the formation in situ of condensed phosphoric acids depending on the condition of the reaction.

Among the esters of phosphoric acids, which can be used in the process of the invention, those which possess one or more free acid groups are preferred. Thus it is possible to use orthophosphates of the general formula:

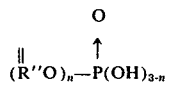
(II)

in which n represents 1 or 2, and R" represents a linear, branched or cyclic hydrocarbon radical containing 1 to 15 carbon atoms, optionally substituted by a group or an atom, which is inert under the conditions of the reaction, such as a nitro or alkoxy group or a halogen atom. Specific examples of radicals R" are alkyl radicals such as methyl, ethyl, propyl, isopropyl, butyl, isobutyl, heptyl and octyl radicals, lower alkyl radicals containing 1 to 4 carbon atoms being preferred; aralkyl radicals such as benzyl and β-phenyl-ethyl radicals; cycloalkyl radicals such as the cyclohexyl radical; and aryl radicals such as phenyl, 2-methyl-phenyl, 2-chlorophenyl and 4-chloro-phenyl radicals. The following orthophosphates are examples of compounds which are particularly suitable: monoethyl, monomethyl, monopropyl, monoisopropyl, monobutyl, monoisobutyl, dimethyl, diethyl, dipropyl, diisopropyl, monobenzyl, dibenzyl, monophenyl, mono-(2-methyl-phenyl), 4-chloro-phenyl, diphenyl, bis-(4-chloro-phenyl), methyl benzyl and propyl benzyl orthophosphates.

It is also possible to use pyrophosphates of the general formula:

$$(R''O)_n - P_2O_3(OH)_{4-n} \quad (III)$$

in which n is 1, 2 or 3 and R'' is as defined above. Examples of such compounds are methyl, diethyl, benzyl, dibenzyl, phenyl and diphenyl pyrophosphates. Acid polyphosphates such as the monomethyl ester of triphosphoric acid can also be used.

Monofluorophosphoric acid, difluorophosphoric acid ($HOPOF_2$) and dichlorophosphoric acid ($HOPOCl_2$) are examples of the halogenophosphoric acids usable in the process of the invention.

Examples of esters of halogenophosphoric acids are halogeno-orthophosphates of the general formula:

$$(X)_n-\overset{\underset{\parallel}{O}}{P}(OR'')_{3-n} \quad (IV)$$

in which n is 1 or 2 an R'' is as defined above, and X represents a halogen atom such as F, Cl or Br. Examples of these compounds are ethyl, hexyl, methyl, propyl, butyl, phenyl, 2-methyl-phenyl, 4-chloro-phenyl and 2-nitro-phenyl dichlorophosphates; dimethyl, diethyl, 2-fluoro-ethyl, phenyl methyl, phenyl propyl, and diphenyl chlorophosphates, and dipropyl, diisopropyl and dicyclohexyl fluorophosphates. It is also possible to use halogenopyrophosphates such as diethyl dichloropyrophosphate, diethyl difluoropyrophosphate and triethyl fluoropyrophosphate. These various esters and the processes for obtaining them have been described in "Methoden der Organischen Chemie," HOUBEN-WEYL, Volume XII/2, "ORGANISCHE Phosphor-Verbindungen," (1964), pages 143 to 943 and in "Phosphorus and its Compounds", Volume I, (1958), J. R. VAN WAZER, $PCl_5$, $POCl_{POCl_3}$, $POF_3$, $POClF_2$ and $POCl_2F$ are preferred examples of the phosphorus halides and oxyhalides.

The amount of phosphorus-containing compound, expressed by the ratio of the number of molecules of hydrogen peroxide to the number of gram atoms of phosphorus employed in the reaction, can vary within wide limits. Thus, when the phosphorus-containing compound is liquid under the reaction conditions, it can form the reaction medium. This is the case in particular for orthophosphoric acid and its aqueous solutions which contain up to 30% by weight of water. In general terms, it is preferable that the ratio $H_2O_2/P$ is 0.1:1 to 50:1, especially 0.5:1 to 10:1.

The amount of hydrogen peroxide employed can generally be of the order of one molecule of $H_2O_2$ per molecule of aromatic compound; it is however preferable not to exceed 0.3 mol of $H_2O_2$ per mol of aromatic compound, and especially 0.15 mol per mol.

The concentration of the aqueous solution of hydrogen peroxide employed is not generally critical. Aqueous solutions of hydrogen peroxide of concentration greater than 20% by weight are very suitable.

The process according to the invention can be carried out at temperatures of 20° to 150°C, and preferably 50° to 120°C, and at pressures greater than or equal to atmospheric pressure.

The reaction can be carried out in the presence of inert organic solvents such as, for example, 1,2-dimethoxyethane, chloroform, acetonitrile and dichloroethane, particularly when the temperature chosen is below the melting point of the aromatic compound.

Hydrogen peroxide and the phorphorus-containing compound can be employed together or separately. They can be introduced gradually or all at once into the aromatic compound (and optionally a solvent), which has been heated to a suitable temperature. For example, it is possible gradually to introduce a mixture of the phosphorus-containing compound and hydrogen peroxide, if necessary heated to the temperature chosen for the reaction, into the aromatic compound.

Examples of aromatic compounds which can be hydroxylated by the process of the invention are phenol, and the various isomeric cresols, anisoles and phenetols.

The process according to the invention makes it possible to obtain excellent yields of the hydroxylation products. Thus hydroquinone and pyrocatechol may be obtained with an overall yield which can be as much as 85% relative to the hydrogen peroxide employed. The process can be adapted easily to continuous operation.

The following Examples illustrate the invention.

EXAMPLE 1

94 g of phenol (1 mol) are introduced into a 250 cm³ 3-necked flask equipped with a stirring system, a reflux condenser, a thermometer and a heating device, and are heated to 100°C. 2.2 g of pyrophosphoric acid (corresponding to 0.0125 mol or 0.025 gram atom of P) are then added and, immediately afterwards, 2.44 g of 68.6% hydrogen peroxide (0.049 mol) are run in all at once.

After 2 hours 30 minutes at 100°C, it is found that the hydrogen peroxide has disappeared completely. The reaction mixture is neutralised by means of an N sodium hydroxide solution in methanol and then the diphenols formed are measured by chromatography.

The following have formed:

2.10 g of pyrocatechol (yield relative to $H_2O_2 = 38.9\%$) and 0.785 g of hydroquinone(yield relative to $H_2O_2 = 14.55\%$).

The overall yield of diphenols is 53.5% relative to $H_2O_2$.

EXAMPLES 2 to 10

The procedure of Example 1 is followed, under the conditions given in the following Table:

| EXAMPLE | T in °C | Duration | Phosphorus-containing compound | Phenol/$H_2O_2$ moles | $H_2O_2$/P moles/g.atom | Yields/$H_2O_2$ % | | |
|---|---|---|---|---|---|---|---|---|
| | | | | | | Hydroquinone | Pyrocatechol | Total |
| 2 | 100 | 3 hrs. | $H_3PO_4$[(1)] | 20 | 2 | 11.2 | 33.4 | 44.6 |
| 3 | 100 | 2 hrs. | $H_4P_2O_7$ | 20 | 2 | 14.5 | 38.9 | 53.4 |
| 4 | 100 | 1hr. 45 mins. | Polyphosphoric | 20 | 2 | 14.7 | 37.3 | 52 |

-continued

| EXAMPLE | T in °C | Duration | Phosphorus-containing compound | Phenol/ $H_2O_2$ moles | $H_2O_2$/P moles/g.atom | Yields/$H_2O_2$ % | | |
|---|---|---|---|---|---|---|---|---|
| | | | | | | Hydroquinone | Pyrocatechol | Total |
| 5 | 100 | 1hr. 15 mins. | acid[2] $H_4P_2O_7+P_2O_5$[3] | 20 | 2 | 16.3 | 40.1 | 56.4 |
| 6 | 100 | 1 hr. | $P_2O_5$ | 20 | 2 | 20.1 | 51.9 | 72 |
| 7 | 100 | 1hr. 45 mins. | $P_2O_5$ | 20 | 4 | 16.7 | 47 | 63.8 |
| 8 | 100 | 3 hrs. | $P_2O_5$ | 20 | 8 | 14.9 | 42.1 | 57 |
| 9 | 100 | 15 mins. | $P_2O_5$ | 20 | 1 | 24.8 | 62.1 | 86.9 |
| 10 | 90 | 30 mins. | $POCl_3$ | 20 | 10 | 5 | 26.6 | 31.6 |

[1] Aqueous solution containing 85% by weight of $H_3PO_4$
[2] Corresponding acid containing 85% by weight of $P_2O_5$
[3] Mixture corresponding to the total containing 91% by weight of $P_2O_5$

EXAMPLE 11

112.8 g of phenol (1.2 mols) and 0.43 g of 90% by weight $H_3PO_4$ are introduced into the apparatus described in Example 1. The contents of the flask are heated to 45°C and to them are added over 20 minutes 36 g of a solution obtained by adding, at a temperature of between 5° and 10°C, 3.77 g of 95.6% by weight $H_2O_2$ (0.106 mol) dissolved in 10 cm³ of acetonitrile containing 0.74 g of water to a solution of 7.1 g of $P_2O_5$ (0.05 mol) in 30 cm³ of acetonitrile and keeping the said solution at 20°C for 3 hours. After the end of the addition, the reaction mixture is kept for a further 30 minutes at 45°C and then the temperature is raised to 60°C for 1 hour 30 minutes. The acetonitrile is removed by distillation and then the reaction mixture is extracted with 150 cm³ of diethyl ether. The extract is washed 4 times with 40 cm³ of distilled water, the organic layer is dried over anhydrous $Na_2SO_4$ and then filtered. The ether is evaporated and the diphenols in the organic residue are measured by chromatography. The yield, expressed relative to the hydrogen peroxide employed, is 37.1% in the case of pyrocatechol and 14% in the case of hydroquinone.

We claim:

1. A process for the preparation of hydroxylated aromatic compound, which consists of hydroxylating a compound of the general formula:

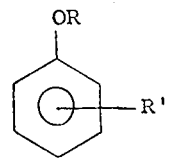

in which each of R and R', which may be the same or different, represents a hydrogen atom or an alkyl radical containing 1 to 4 carbon atoms, at a temperature from 20° to 150°C., with a reagent consisting of hydrogen peroxide in the presence of phosphorus pentoxide, the molar ratio of hydrogen peroxide to the aromatic compound being not more than 0.3:1 and the ratio of the number of molecules of hydrogen peroxide to the number of gram atoms of phosphorus in the phosphorus pentoxide being from 0.5:1 to 10:1.

2. A process according to claim 1, wherein the compound, which is hydroxylated, is phenol or a cresol, anisole or phenetol.

3. A process according to claim 1 which comprises hydroxylating phenol at 90°– 100°C. for 15 minutes to 3 hours with 0.05 mol hydrogen peroxide per mol of phenol and phosphorus pentoxide, the ratio of the number of molecules of hydrogen peroxide to the number of g atoms of phosphorus in the phosphorus pentoxide being 1:1 to 10:1.

* * * * *